US008625195B2

(12) United States Patent
Lin et al.

(10) Patent No.: US 8,625,195 B2
(45) Date of Patent: Jan. 7, 2014

(54) OBJECTIVE-TYPE DARK-FIELD ILLUMINATION DEVICE FOR MICROFLUIDIC CHANNEL

(75) Inventors: Che-hsin Lin, Kaohsiung (TW); Shi-wei Lin, Tainan (TW); Jui-hung Hsu, Kaohsiung (TW); Chih-han Chang, Tainan (TW)

(73) Assignee: National Sun Yat-Sen University, Kaohsiung (TW)

( * ) Notice: Subject to any disclaimer, the term of this patent is extended or adjusted under 35 U.S.C. 154(b) by 385 days.

(21) Appl. No.: 12/851,535

(22) Filed: Aug. 5, 2010

(65) Prior Publication Data

US 2011/0157692 A1    Jun. 30, 2011

(30) Foreign Application Priority Data

Dec. 30, 2009    (TW) .............................. 98145966 A

(51) Int. Cl.
*G02B 21/10*    (2006.01)
(52) U.S. Cl.
CPC .................................... G02B 21/10 (2013.01)
USPC ......................................... 359/387; 359/398
(58) Field of Classification Search
CPC ........................................................ G02B 21/10
USPC ................................................ 359/387, 398
See application file for complete search history.

(56) References Cited

U.S. PATENT DOCUMENTS

| | | | | |
|---|---|---|---|---|
| 4,175,839 A | * | 11/1979 | Muller et al. | 351/214 |
| 5,430,541 A | * | 7/1995 | Sapp et al. | 356/246 |
| 5,831,736 A | * | 11/1998 | Lichtman et al. | 359/389 |
| 6,259,557 B1 | | 7/2001 | Miyashita et al. | |
| 6,753,970 B1 | * | 6/2004 | Neumann et al. | 356/600 |
| 7,106,503 B2 | * | 9/2006 | Vodyanoy et al. | 359/387 |
| 7,224,524 B2 | * | 5/2007 | Tsuchiya et al. | 359/387 |
| 7,369,233 B2 | * | 5/2008 | Nikoonahad et al. | 356/369 |
| 7,688,505 B2 | * | 3/2010 | Vodyanoy et al. | 359/387 |
| 7,695,683 B2 | * | 4/2010 | Quan et al. | 422/504 |
| 2002/0191281 A1 | * | 12/2002 | Osa et al. | 359/387 |

OTHER PUBLICATIONS

Davis, Christopher C. Lasers and Electro-optics: Fundamentals and Engineering. Cambridge [England: Cambridge UP, 1996. 389. Print.*

* cited by examiner

*Primary Examiner* — Zachary Wilkes
(74) *Attorney, Agent, or Firm* — Cheng-Ju Chiang

(57) ABSTRACT

An objective-type dark-field illumination device for a microfluidic channel is provided and includes an optical stop having a pair of symmetric curved slits used to adjust the optical path and inner numerical aperture of a dark-field light source generated by the device. The dark-field illumination can focus on a smaller spot to illuminate a sample in the microfluidic channel by matching a pin-hole combined with a transmitter objective lens. The optical path and smaller spot is advantageous to solve the problem of a traditional dark-field illumination that may generate background light noise scattered from inner walls of the microfluidic channel to lower the image contrast. Therefore, the signal or image resolution of capturing the scattered light and/or emitted fluorescent light emitted from the sample in the microfluidic channel can be enhanced. Meanwhile, the device can simultaneously excite and detect multiple fluorescent samples with different excited wavelengths in the microfluidic channel.

20 Claims, 7 Drawing Sheets

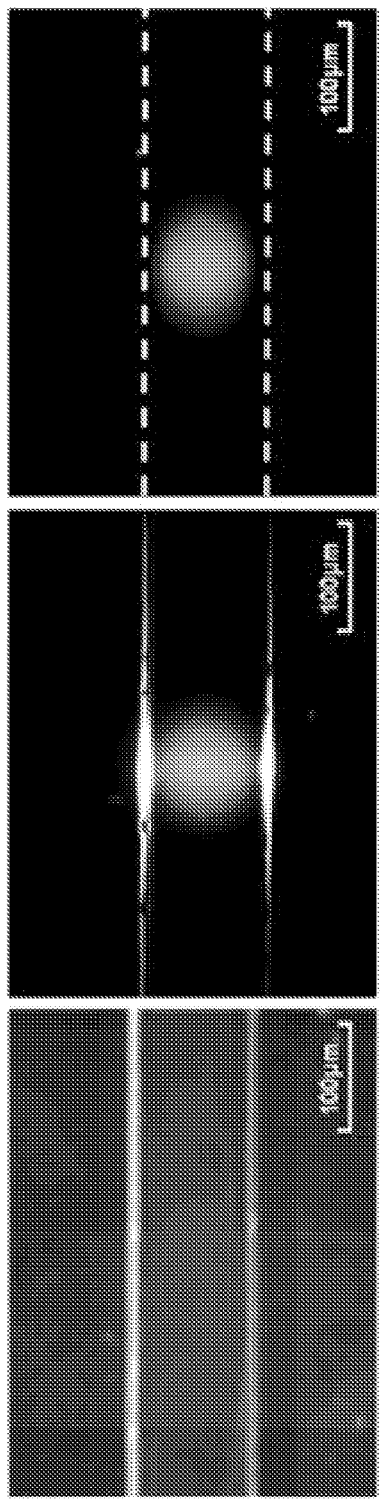
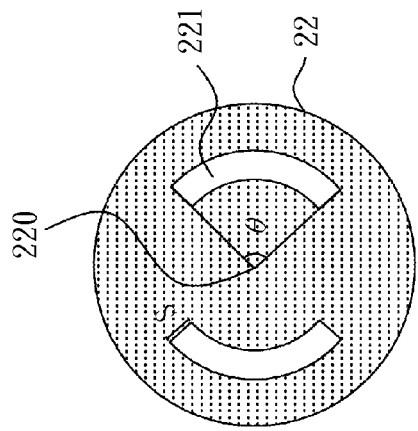
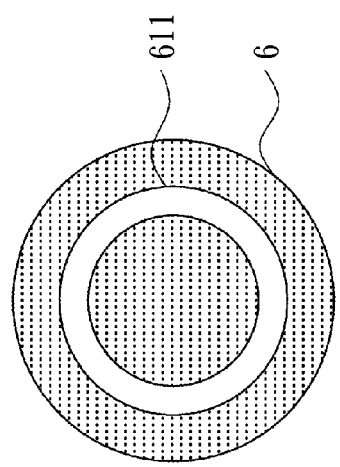
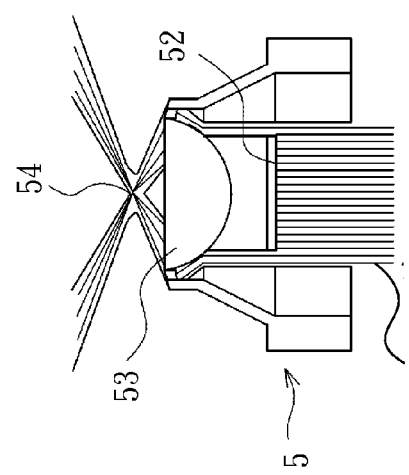
Fig. 4A
Fig. 4B
Fig. 4C

OBJECTIVE-TYPE DARK-FIELD ILLUMINATION DEVICE FOR MICROFLUIDIC CHANNEL

FIELD OF THE INVENTION

The present invention relates to an objective-type dark-field illumination device for a microfluidic channel, and more particularly to an objective-type dark-field illumination device which includes an optical stop having a pair of symmetric curved slits to adjust the light path field for producing a pair of parallel light with curved profile, and combines with a transmitter objective lens to generate a dark-field illumination for illuminating a tested sample in a microfluidic channel by a smaller focused spot due to a small pin-hole.

BACKGROUND OF THE INVENTION

A traditional dark-field illumination system is used to observe an un-stained semi-transparent material (such as cells, micro-algae or other biological samples) in a transparent medium. The main technology of the dark-field illumination system is based on the principle that scattered and reflective light will be generated when a light passes through a sample substance, and thus the system can only receive the scattered light and a portion of the reflective light by changing the relative angle and position of an observer and a light detection device. Thus, the scattered light and reflective light provide information-rich signals including the profile, the structural variation and the refraction variation.

A dark-field condenser is a common accessory used in a microscope system, wherein the dark-field condenser is co-axially disposed on a light path to generate a hollow-cone illumination for observing micro-particles, micro-pore defect structures or other to-be-observed micro-structures in a transparent medium. A traditional dark-field condenser comprises a positive lens and a circular optical stop. Further, the dark-field condenser can further comprise a reflective mirror or a curved mirror, in order to increase the numerical aperture (N.A.). However, although the foregoing co-axial dark-field focusing method can change the light path by various manners, most of the light path is an annular light field.

For example, U.S. Pat. No. 6,259,557 disclosed a traditional device and method for dark field illumination, as shown in FIG. 1, wherein the device comprises: a light source 11 to provide light, two light collection lenses 12a, 12b to collect the light, a pin-hole stop 13 having a pin-hole 131 to form a light source spot, a field lens 14 through which the light source spot passes to form parallel light, a ring diaphragm 15 having a ring slit 151 through which the parallel light passes, a ring-shape reflection mirror 16 to reflect the parallel light, a fly-eye optical device 17 through which the reflected parallel light passes to form even annular light, and a ring-shape condenser lens 18 through which the annular light passes to form a spot which focuses on a focal plane 19 of an objective lens(not-shown). The purpose of the dark field illumination is to evenly emit light onto the surface of the sample, and to provide higher brightness and contrast image for satisfying needs of observing reflective samples. The focused spot still forms a relatively large excitation region of a diameter about 4-8 mm on the focal plane 19 of the objective lens.

However, because the traditional device of dark field illumination is generally used to satisfy needs of large excitation region and high numerical aperture for image observation, the excitation spot focused by the traditional device is greater than the size scale of 100 micrometer ($\mu m$). Thus, when the focal plane 19 is located within a microfluidic channel of a microfluidic chip and the width of the microfluidic channel and samples therein are smaller than 100 $\mu m$, the excitation spot focused by the traditional device will be greater than the width of the microfluidic channel and samples therein. As a result, the excitation spot may illuminate inner walls of the microfluidic channel to cause a large number of background noise due to the scattering of the channel wall, so that the traditional device cannot provide a suitable dark-field illumination for clearly observing the samples in the microfluidic channel.

Therefore, it is necessary to provide an objective-type dark-field illumination device for a microfluidic channel to solve the foregoing problems, as described above.

SUMMARY OF THE INVENTION

A primary object of the present invention is to provide an objective-type dark-field illumination device for detecting samples in a microfluidic channel, which includes: an optical stop having a pair of symmetric curved slits used to adjust the optical path and inner numerical aperture (N.A.) of a dark-field light source generated by the device; the outer N.A. is determined by the match of a high N.A. of an excited objective lens; the inner N.A. and the outer N.A. of the dark-field illumination can be adjusted to determine the path of the excitation light by the optical stop pattern. As a result, the path behavior of this invented dark-field illumination can be conveniently and rapidly adjusted for illuminating a tested sample in a microfluidic channel, while the device is advantageous to efficiently solve the problem of a traditional dark-field illumination that may generate noise scattered from inner walls of the microfluidic channel to lower the image contrast. Therefore, the signal resolution of capturing the scattered light and/or emitted fluorescence from the tested sample in the microfluidic channel during observation can be enhanced. Meanwhile, the device can simultaneously detect various fluorescent samples with different excited wavelengths in the microfluidic channel.

A secondary object of the present invention is to provide an objective-type dark-field illumination device for sample detection in a microfluidic channel, which uses a pair of symmetric curved slits to generate a dark-field illumination, and rapidly adjusts the size of the spot by changing the size of the pin-hole, so that the installation structure of the dark-field illumination device can be simplified, the control convenience of adjusting the spot size can be enhanced, and the cost of purchase, repair and design change can be lowered.

To achieve the above object, the objective-type dark-field illumination device for detecting sample in a microfluidic channel of a preferred embodiment of the present invention comprises: a parallel light source assembly for generating a parallel light; an optical stop having a pair of curved slits arranged along a direction parallel to an extension direction of a microfluidic channel, wherein the parallel light passes through the two curved slits to generate two curved parallel light; and a transmitter objective lens with high numerical aperture (N.A.) for converting the two curved parallel light into two curved conical illumination focusing on a spot in the microfluidic channel, so as to illuminate tested samples in the microfluidic channel and to lower the light scattering behavior of inner walls of the microfluidic channel, wherein the diameter of the spot is smaller than or equal to the width of the inner walls of the microfluidic channel.

In one embodiment of the present invention, the size of the two curved slits is equal to each other and the two curved slits are symmetrically arranged on the optical stop.

In one embodiment of the present invention, each of the two curved slits has two ends by defining an included angle in relation to a geometric center of the optical stop, and the included angle is ranged between 60 and 90 degree, such as 80 degree.

In one embodiment of the present invention, each of the two curved slits has a radial width equal to or smaller than 3 millimeter (mm), such as 2 mm.

In one embodiment of the present invention, the parallel light source assembly comprises a continuous light source, a condenser lens, a pin-hole stop, a reflective mirror and a field lens in turn.

In one embodiment of the present invention, the pin-hole stop has a pin-hole, and the diameter of the pin-hole is ranged between 0.1 and 2 mm, such as 1 mm.

In one embodiment of the present invention, the pin-hole size is a factor to determine the diameter of the excitation spot which is varied by adjusting the diameter of pin-hole.

In one embodiment of the present invention, the N.A. value of the transmitter objective lens is ranged between 0.7 and 1.2, such as 0.75.

In one embodiment of the present invention, an entrance pupil of the transmitter objective lens is ranged between 10 to 20 mm, such as 15 mm.

In one embodiment of the present invention, the diameter of the excitation spot is smaller than 100 µm.

In one embodiment of the present invention, the present invention further comprises a receiver objective lens with low numerical aperture (N.A.) for receiving scattered light and/or emitted fluorescence from sample passing through the interrogated region in the microfluidic channel.

In one embodiment of the present invention, the N.A. value of the receiver objective lens, such as 0.45, is smaller than that of the transmitter objective lens.

In one embodiment of the present invention, the receiver objective lens further guides the received scattered light and/or emitted fluorescence from samples into an optical detection system, such as charge-coupled device (CCD), photomultipliers (PMT), spectrometer or spectrophotometer.

In one embodiment of the present invention, the radial width s of the curved slits is determined according to equations (I) and (II), as follows:

$$D_i = 2(N.A.)(f_o) \quad (I);$$

$$s = (D_o - D_i)/2 \quad (II);$$

wherein N.A. is an numerical aperture value of the receiver objective lens; $f_o$ is a focal length of the transmitter objective lens; $D_i$ is the calculated entrance pupil of the transmitter objective lens when N.A. is equal to the receiver objective lens or an inner diameter of the curved slits; $D_0$ is the entrance pupil of the transmitter objective lens or an outer diameter of the curved slits; and s is the radial width of the curved slits.

In one embodiment of the present invention, the optical detection system is a spectrometer or a spectrophotometer, and the parallel light is a light source with continuous wavelength, so that the optical detection system can simultaneously excite and detect multiple emitted fluorescent signals of at least two fluorescent colors with at least two fluorescent samples.

DESCRIPTION OF THE DRAWINGS

The structure and the technical means adopted by the present invention to achieve the above and other objects can be best understood by referring to the following detailed description of the preferred embodiments and the accompanying drawings, wherein:

FIGS. 4A, 4B and 4C are schematic views of a first traditional dark-field illumination device, a second traditional dark-field illumination device with a ring-style stop and the objective-type dark-field illumination device according to the preferred embodiment of the present invention, each of which provides a dark-field illumination and has a receiver objective lens to receive scattered light (or emitted fluorescent light) from samples and guide it into an optical detection system (such as a CCD camera) for generating microscopic photographs of the microfluidic channel, wherein flowing liquid in the microfluidic channel contains fluorescent tags which are used to simulate the tested sample;

DETAILED DESCRIPTION OF THE PREFERRED EMBODIMENTS

Figure 1:
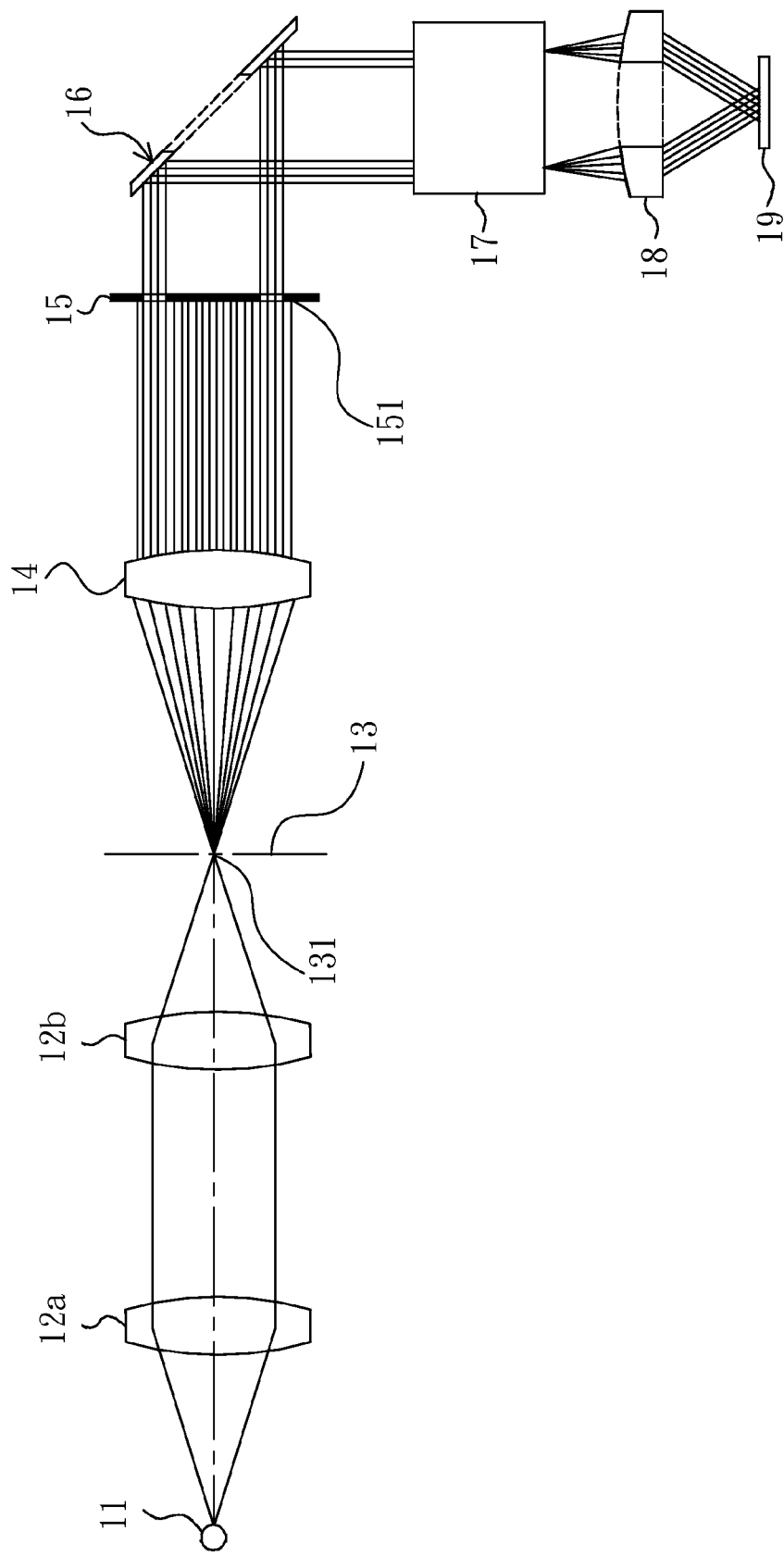
FIG. 1 is an operational view of a traditional dark-field illumination device.

Referring now to FIGS. 2, 2A, 2B and 3, an objective-type dark-field illumination device for a microfluidic channel according to a preferred embodiment of the present invention is illustrated. As shown, an objective-type dark-field illumination device 2 is generally provided on a first side of a microfluidic chip 3, wherein the dark-field illumination device 2 comprises a parallel light source assembly 21, an optical stop 22 and a transmitter objective lens 23 with high numerical aperture (N.A.). The dark-field illumination device 2 is used to provide a suitable dark-field illumination to illuminate samples 32 in a microfluidic channel 31 of the microfluidic chip 3, so as to considerably lower background light noise scattered from inner walls of the microfluidic channel 31 for the purpose of increasing the contrast and signal/noise ratio of sample images and detection signals. In addition, a receiver objective lens 4 is provided on a second side of the microfluidic chip 3 to receive the signals (such as images, scattered light, emitted fluorescence) from samples with high contrast and low noise.

Figure 2:
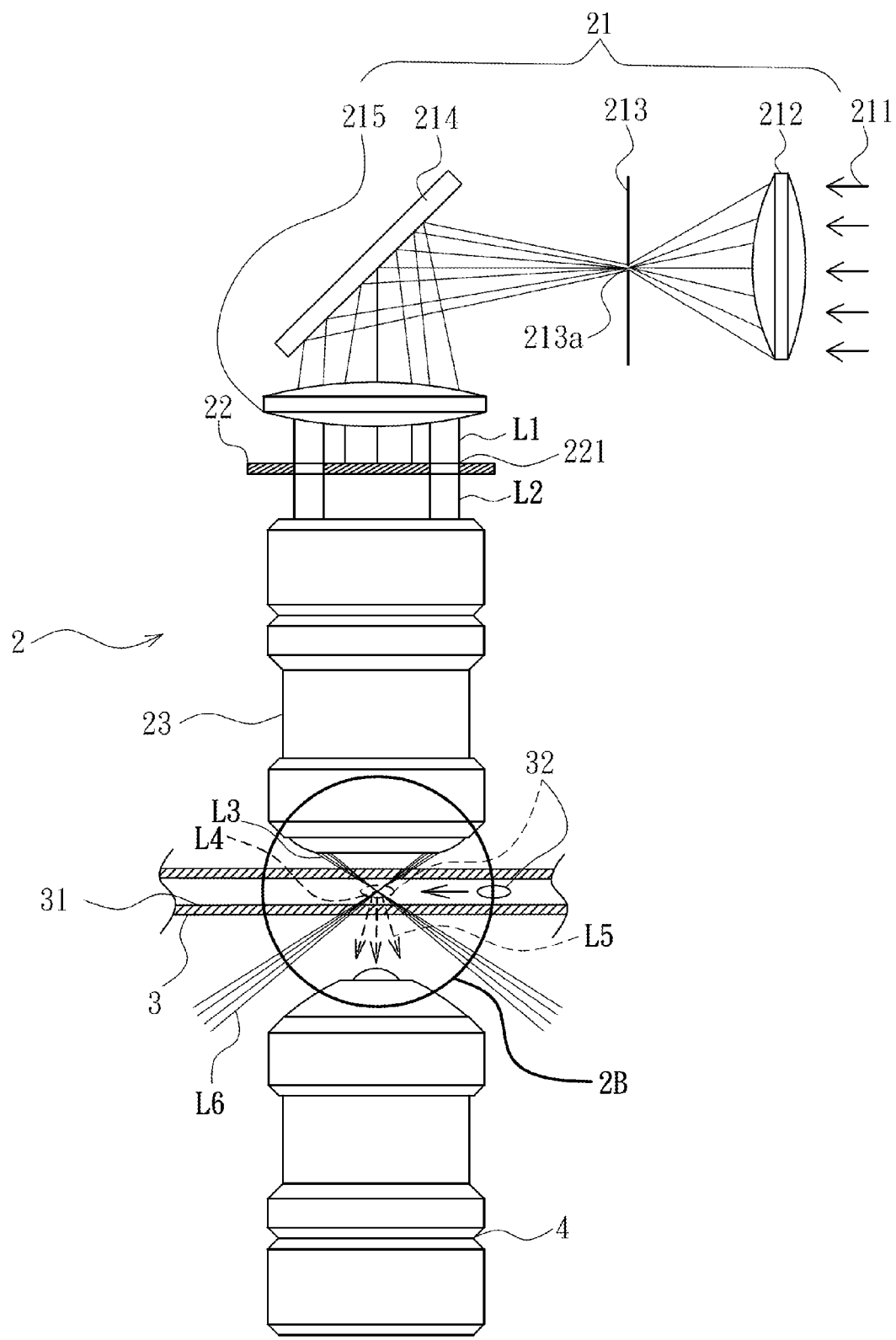
FIG. 2 is an operational view of an objective-type dark-field illumination device for a microfluidic channel according to a preferred embodiment of the present invention.

Referring now to FIG. 2, in the preferred embodiment of the present invention, the objective-type dark-field illumination device 2 is installed in an inverted optical microscope (not shown), wherein the parallel light source assembly 21 can be an existed element in the inverted optical microscope. In the embodiment, the parallel light source assembly 21 is used to generate a parallel light L1, wherein the parallel light assembly 21 comprises a continuous light source 211, a condenser lens 212, a pin-hole stop 213, a reflective mirror 214 and a field lens 215 in turn. The continuous light source 211 can be selected from continuous light generated by a 100 W tungsten lamp. The condenser lens 212 is generally a convex lens, wherein the continuous light source 211 passes through the condenser lens 212 to focus on a plane of a pin-hole 213a of the pin-hole stop 213, wherein the diameter of the pin-hole 213a is ranged between 0.1 and 2 mm, such as preferably 1 mm. After the continuous light source 211 passes through the pin-hole 213a, the continuous light source 211 radiates onto the reflective mirror 214, and then reflects to pass through the field lens 215, so as to generate the parallel light L1, wherein the field lens 215 can be a convex lens, while the position of the pin-hole 213a is located on a focal plane of the condenser lens 212 and the field lens 215.

Figure 2A:
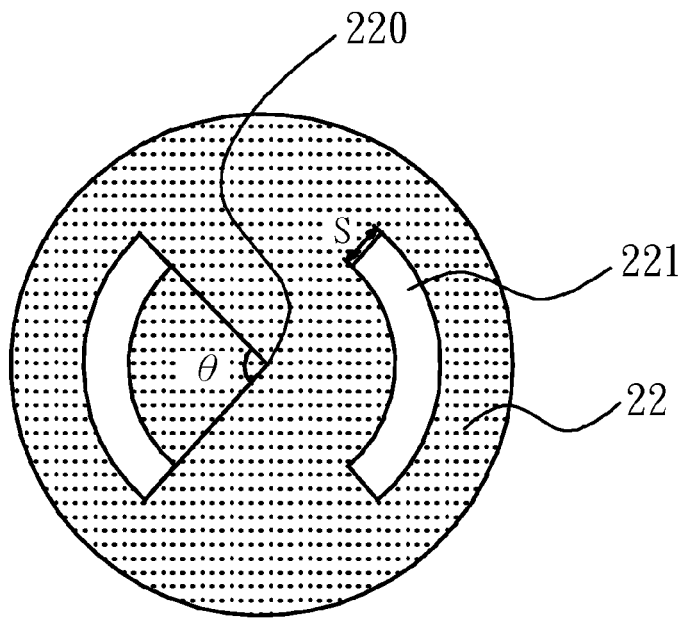
FIG. 2A is a top view of an optical stop having a pair of symmetric curved slits according to the preferred embodiment of the present invention.

Referring now to FIGS. 2 and 2A, in the preferred embodiment of the present invention, the optical stop 22 has two curved slits 221, wherein the size of the two curved slits 221 is equal to each other and the two curved slits 221 are symmetrically arranged on the optical stop 22. In the embodiment, the optical stop 22 is a transparent plastic plate which is printed with a dark ink pattern on the surface thereof to pattern two curved transparent regions without being covered by the dark ink, so as to define the two curved slits 221. Alternatively, the transparent plastic plate can be entirely printed with the dark ink, and then cut to form two curved through holes by a cutter or laser, so as to define the two curved slits 221. The foregoing manufacturing method of plastic photomask can advantageously lower the manufacture cost of the optical stop 22. After manufacturing, the optical stop 22 is used to adjust an optical path for entering the transmitter objective lens 23. In other words, the parallel light L1 of the parallel light source assembly 21 can pass through the two curved slits 221 to form two curved parallel light L2, and then the two curved parallel light L2 enters the transmitter objective lens 23. Furthermore, the two curved slits 221 are arranged along a direction (such as a direction from right to left of FIG. 2) parallel to an extension direction of the microfluidic channel 31 in the microfluidic chip 3 (such as a direction from right to left of FIG. 2). As shown in FIG. 2A, each of the two curved slits 221 has two ends by defining an included angle θ in relation to a geometric center 220 of the optical stop 22, and the included angle θ is ranged between 60 and 90 degree, such as preferably 80 degree. Meanwhile, each of the two curved slits 221 has a radial width s which is equal to or smaller than 3 mm, such as 2 mm. For the optical stop 22, the radial width s and the included angle θ of the two curved slits 221 can be used to vary an optical path of dark-field illumination, wherein the radial width s can vary the inner numerical aperture (N.A.) of dark-field illumination, while the included angle θ can vary the direction of the optical path of dark-field illumination, which will be described more detailed hereinafter.

Figure 2B:
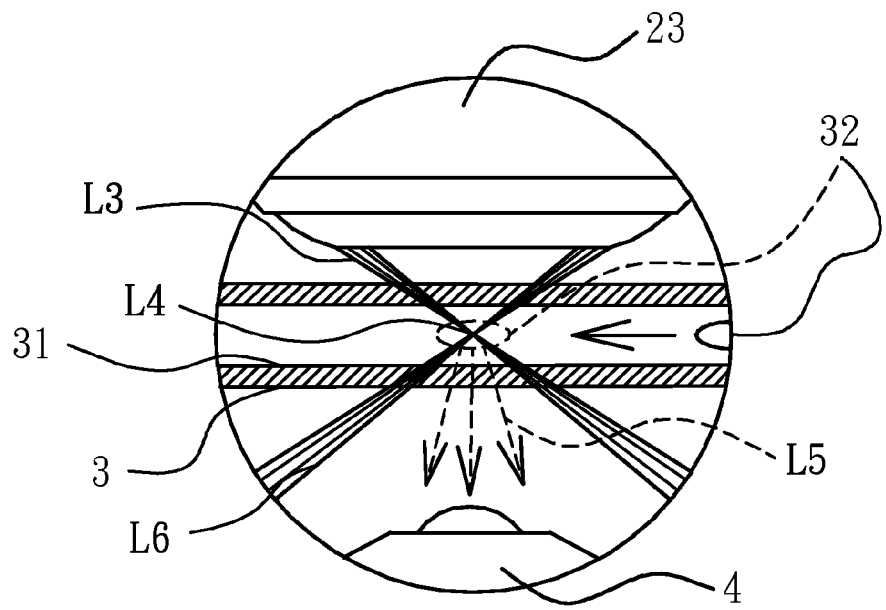
FIG. 2B is a partial enlarged view of a tested sample particle in the microfluidic channel of FIG. 2.
Figure 3:
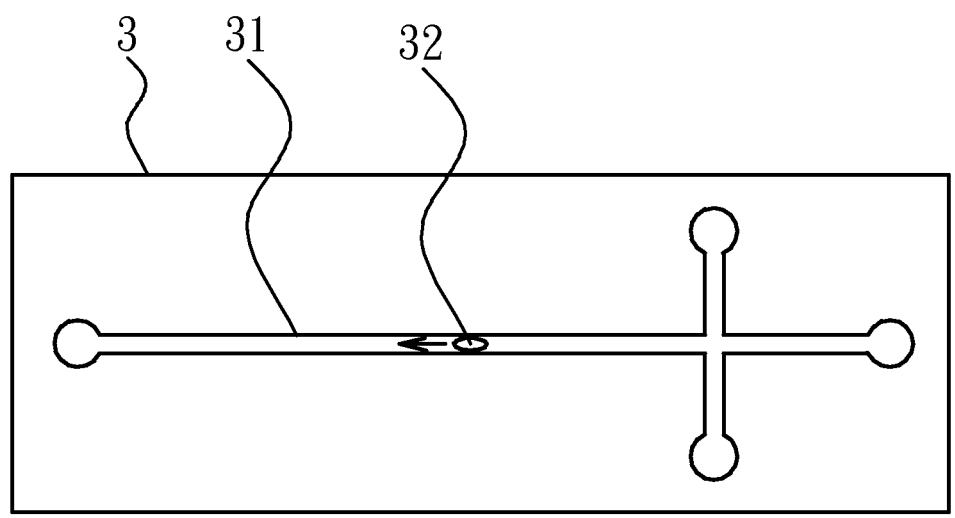
FIG. 3 is a top view of a microfluidic chip having the microfluidic channel according to the preferred embodiment of the present invention.

Referring to FIGS. 2, 2B and 3, in the preferred embodiment of the present invention, the transmitter objective lens 23 is a microscope objective lens of high numerical aperture (N.A.). In the embodiment, the N.A. value of the transmitter objective lens 23 is ranged between 0.7 and 1.2, such as preferably 0.75. An entrance pupil of the transmitter objective lens 23 is ranged between 10 to 20 mm, such as preferably 15 mm. Moreover, the rate of the transmitter objective lens 23 is 20×, the working distance (W.D.) thereof is 1 mm, and the focal length ($f_0$) thereof is 10 mm. The transmitter objective lens 23 is used to change the optical path of dark-field illumination after being focused, i.e. to convert the two inputted curved parallel light L2 into two curved conical light L3. The two curved conical light L3 can be focus on a spot L4 in the microfluidic channel 31 of the microfluidic chip 3 for illuminating a tested sample 32 in the microfluidic channel 31 and forming a plurality of scattered light (or emitted fluorescent light) from samples L5. In the present invention, because the two curved slits 221 are arranged along a direction parallel to the extension direction of the microfluidic channel 31 in the microfluidic chip 3 and the radial width s and the included angle θ of the two curved slits 221 can be suitably controlled to vary an optical path of dark-field illumination. In the present invention, the diameter of the spot L4 is set according to the width of the inner walls of the microfluidic channel 31. In the present invention, the pin-hole 213a with a diameter of 1 mm can form the spot L4 with a diameter of about 100 μm, so that the diameter of the spot L4 can be smaller than or equal to the width of the inner walls of the microfluidic channel 31. As a result, the two curved slits 221 of the present invention can efficiently solve the problem of a traditional dark-field light source that may generate background noise scattered from inner walls of the microfluidic channel to lower the image contrast. Thus, during observation, the signal resolution of capturing the scattered light L5 (and/or emitted fluorescent light) from the tested sample 32 in the microfluidic channel 31 can be enhanced.

Referring to FIGS. 2, 2B and 3, in the preferred embodiment of the present invention, the microfluidic channel 3 can be selected from various types of biochips or detection chips having at least one microfluidic channel 31, but the present invention is not limited to the shape of the microfluidic channel 3 or the microfluidic channel 31 and the type of the tested sample 32. Only if the substrate of the microfluidic channel 3 is transparent for light to pass through the microfluidic channel 31, the type of the microfluidic channel 3 can be applied to the present invention, so that the objective-type dark-field illumination device 2 of the present invention can provide a dark-field light source to illuminate the tested sample 32 in the microfluidic channel 31. The tested sample 32 can be selected from various biological or chemical samples, such as cells, organelles, bacteria or nano-microspheres; or cells, organelles, bacteria, virus, protein microparticles or DNA fragments having nano-microspheres or fluorescent tags, but not limited thereto. Furthermore, according to light type needed by the tested sample 32 (such as white light, single color light, lasers and etc.), the parallel light source assembly 21 can correspondingly change the bulb type of the continuous light source 211, or additionally add a filter, in order to satisfy the optical detection need of the tested sample 32.

Referring still to FIG. 2, the preferred embodiment of the present invention further comprises a receiver objective lens 4 with low numerical aperture (N.A.), such as a microscope objective lens of low numerical aperture (N.A.). In the embodiment, the N.A. value of the receiver objective lens 4, such as 0.45, is smaller than that of the transmitter objective lens 23. Moreover, the rate of the receiver objective lens 4 is 20×, the working distance (W.D.) thereof is 1 mm, and the focal length ($f_0$) thereof is 10 mm. The receiver objective lens 4 with low N.A. is used to receive the scattered light (or excited fluorescent light) L5 of the tested sample 32 passed through the microfluidic channel 31. Then, the receiver objective lens 4 can further guide the scattered light (and/or emitted fluorescent light) L5 into an optical detection system, such as charge-coupled device (CCD), photomultipliers (PMT), spectrometer or spectrophotometer for executing the analysis of images, light intensity, spectrum or spectrophotometry.

Referring to FIGS. 2, 2A and 2B, in the preferred embodiment of the present invention, the radial width s of the two curved slits 221 can vary the inner numerical aperture (N.A.) of dark-field illumination, while the included angle θ of the two curved slits 221 can vary the direction of the optical path of dark-field illumination, wherein the radial width s of the curved slits 221 is determined according to equations (I) and (II), as follows:

$$D_i=2(N.A.)(f_o) \qquad (I);$$

$$s=(D_o-D_i)/2 \qquad (II);$$

wherein N.A. is an numerical aperture value of the receiver objective lens 4; $f_o$ is a focal length of the receiver objective lens 4; $D_i$ is the calculated entrance pupil of the transmitter objective lens 23 when N.A. is equal to the receiver objective lens 4 or an inner diameter of the curved slits 221; $D_0$ is the entrance pupil of the transmitter objective lens 23 or an outer diameter of the curved slits 221; and s is the radial width of the curved slits 221. The N.A. value of the transmitter objective lens 23 is greater than that of the N.A. value of the receiver objective lens 4, so that it can prevent the receiver objective lens 4 from receiving unnecessary emitting light L6, and thus the receiver objective lens 4 can simply receive the scattered light (and/or excited fluorescent light) L5 of the tested sample 32 for analysis without background light noise.

For example, when the N.A. value of the receiver objective lens 4 can be 0.45 and the focal length ($f_0$) of the transmitter objective lens thereof is 10 mm, the calculated entrance pupil of the transmitter objective lens 23 when N.A. is equal to the receiver objective lens 4 or the inner diameter of the curved slits 221 can be:

$$D_i=2(N.A.)(f_0)=2(0.45)(10)=9 \text{ mm}$$

In addition, when the entrance pupil of the transmitter objective lens 23 or the outer diameter of the curved slits 221 (i.e. the value $D_0$) is 15 mm, the radial width s of the curved slits 221 can be:

$$s=(D_o-D_i)/2=(15-9)/2=3 \text{ mm}$$

In the present invention, the radial width s is preferably 2 mm, while the included angle θ of the curved slits 221 is preferably 80 degree. The diameter of the spot L4 in the present invention can be smaller than 100 μm, so as to be suitably applied to various microfluidic channels 31 with an wall width W greater than or equal to the diameter of the spot L4 for providing maximum luminous flux and minimum background light noise, i.e. the present invention allows the scattered light (and/or emitted fluorescent light) L5 of the tested sample 32 to have optimal contrast. Moreover, when the objective-type dark-field illumination device 2 is applied to another microfluidic channels 31 with different wall width W, the present invention can change the radial width s of the two curved slits 221 to generate a suitable optical path and a dark-field light source with a smaller spot L4, and also can adjust the size of the pin-hole 213a of the pin-hole stop 213 to rapidly change the diameter of the spot L4. Therefore, in the present invention, the design of the two symmetrical curved slits 221 of the optical stop 22 can advantageously simplify the installation structure of the objective-type dark-field illumination device 2, enhance the control convenience of adjusting the size of the spot L4, and lower the cost of purchase, repair and design change of the dark-field illumination device 2.

Referring now to FIGS. 3, 4A, 4B and 4C, FIGS. 4A, 4B and 4C illustrate schematic views of a first traditional dark-field illumination device, a second traditional dark-field illumination device with ring-style stop and the objective-type dark-field illumination device 2 according to the preferred embodiment of the present invention, each of which provides a dark-field illumination and has a receiver objective lens 4 to receive scattered light (or excited fluorescent light) L5 and guide it into an optical detection system (such as a CCD camera) for generating microscopic photographs of the microfluidic channel 31, wherein flowing liquid in the microfluidic channel 31 contains fluorescent tags which are used to simulate the tested sample 32.

Referring now to FIGS. 3 and 4A, a first traditional dark-field illumination device 5 comprises a continuous light source 51, a patterned stop 52 and a condenser unit 53, wherein the continuous light source 51 passes through the patterned stop 52 to form a ring-shape parallel light source which then passes through the condenser unit 53 to form a ring-shape conical light source to focus on a spot 54. However, the diameter of the spot 54 is considerably greater than the wall width W of the microfluidic channel 31, such that the focusing effect of the spot 54 is poor. As a result, the liquid in the microfluidic channel 31 is excited to generate an image with excess fluorescent light intensity, and a large number of background light noise is scattered from the inner wall of the microfluidic channel 31 and the surface of the microfluidic chip 3, resulting in considerably lowering the optical contrast of the image.

Referring now to FIGS. 3 and 4B, a second traditional dark-field illumination device is similar to the objective-type dark-field illumination device 2 of the present invention, but an optical stop 6 of the second traditional dark-field illumination device only has a ring-shape slit 61. In comparison with the spot 54 of FIG. 4A, the ring-shape slit 61 generates a dark-field light source having a size relatively smaller than that of the focused spot 54 to enhance the image contrast inside/outside the microfluidic channel 31. However, the background light noise scattered from inner walls of the microfluidic channel 31 is still considerable and thus lowers the signal/noise ratio of the tested sample 32 in the microfluidic channel 31 during detection.

In contrast, referring to FIGS. 3 and 4C, the optical stop 22 of the objective-type dark-field illumination device 2 of the present invention has the two symmetrical curved slits 221 arranged along a direction parallel to an extension direction of the microfluidic channel 31 of the microfluidic chip 3, while the radial width s and the included angle θ of the two curved slits 221 can be suitably controlled to vary the optical path of dark-field light source. Thus, the present invention can eliminate the background light noise scattered from the inner walls of the microfluidic channel 31 to prevent the two curved conical light source L3 from being orthogonal to the inner walls and thus generating the background scattered light noise to lower the contrast. As a result, it is advantageous to enhance the image resolution of capturing the scattered light (and/or emitted fluorescent light) L5 emitted from the tested sample 32 in the microfluidic channel 31 by the receiver objective lens 4 with low N.A. during observation.

Figure 5:
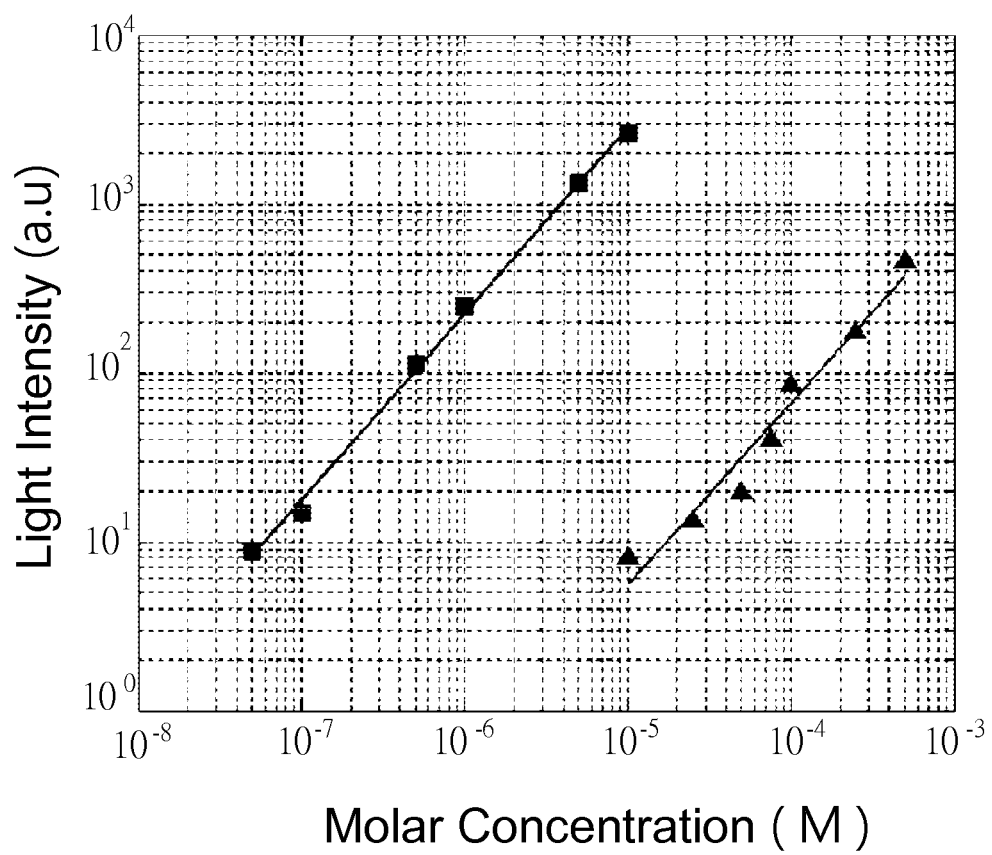
FIG. 5 is a curve diagram of light intensity (a.u.) and molar concentration (M) of the tested sample by using the first traditional dark-field illumination device (represented by "▲") and the objective-type dark-field illumination device according to the preferred embodiment of the present invention (represented by "■"), each of which provides the dark-field illumination and has the receiver objective lens to receive scattered light (or emitted fluorescent light) from samples and guide it into the optical detection system (such as a photomultipliers) for obtaining the light intensity (a.u.) of the tested sample, wherein a plurality of liquids containing different molar concentration (M) of fluorescent tags are used to simulate the tested sample.

Referring now to FIG. 5, it illustrates a curve diagram of light intensity (a.u.) and molar concentration (M) of the tested sample by using the first traditional dark-field illumination device 5 (represented by "▲") and the objective-type dark-field illumination device 2 according to the preferred embodiment of the present invention (represented by "■"), each of which provides the dark-field illumination and has the receiver objective 4 to receive scattered light (or excited fluorescent light) L5 and guide it into the optical detection system (such as a photomultipliers) for obtaining the light intensity (a.u.) of the tested sample 32, wherein a plurality of liquids containing different molar concentration (M) of fluorescent tags are used to simulate the tested sample 32. As shown in FIG. 5, the objective-type dark-field illumination device 2 of the present invention has the two symmetrical curved slits 221 which can relatively enhance the detection sensitivity of the tested sample 32 with low molar concentration, and thus can apparently increase the light intensity signal and the detection threshold of the fluorescent tags in the microfluidic channel 31.

Figure 6:
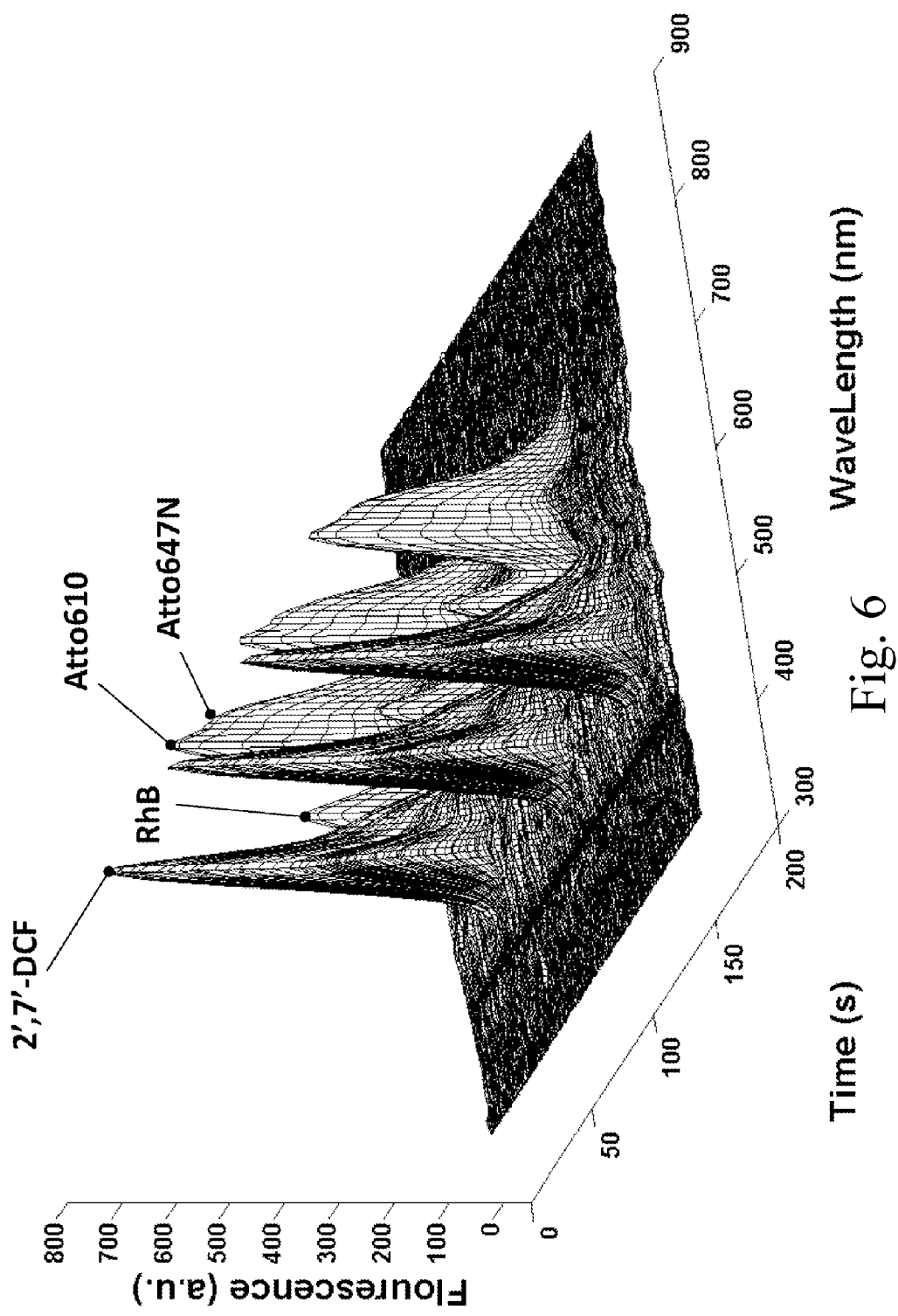
FIG. 6 is a curve diagram of electrophoresis detection of the time (sec), wavelength (nm) and fluorescent intensity (a.u.) of four fluorescent samples having four fluorescent tags with different emitted wavelengths in the microfluidic channel continuously detected by the optical detection system (selected from spectrometer or spectrophotometer) and the objective-type dark-field illumination device according to the preferred embodiment of the present invention which uses a light source of continuous wavelengths.

Referring now to FIG. 6, it illustrates a curve diagram of electrophoresis detection of the time (sec), wavelength (nm) and fluorescent intensity (a.u.) of four fluorescent samples having four fluorescent tags with different wavelengths in the microfluidic channel 31 continuously detected by the optical detection system and the objective-type dark-field illumination device 2 according to the preferred embodiment of the present invention which uses a light source of continuous wavelengths, wherein the four fluorescent tags are 2,7-DCF (max excitation wavelength: 495 nm; max emission wavelength: 525 nm), RhB (max excitation wavelength: 543 nm; max emission wavelength: 578 nm), Atto610 (max excitation wavelength: 608 nm; max emission wavelength: 634 nm) and Atto647N (max excitation wavelength: 648 nm; max emission wavelength: 668 nm), while the downstream of the receiver objective lens 4 is a optical detection system selected from spectrometer or spectrophotometer. Because the excitation light L6 does not directly enter the receiver objective lens 4, the receiver objective lens 4 can only detect the emitted fluorescent signals from the four fluorescent tags. Thus, it can directly and simultaneously obtain multiple fluorescent signals without adding any expensive optical filter. Because the light source of continuous wavelengths is used to excite the four or more fluorescent tags simultaneously, the dark-field illumination device 2 of the present invention can simultaneously detect various mixed fluorescent samples with different excited wavelengths in the microfluidic channel 31 by a single detection operation.

The present invention has been described with a preferred embodiment thereof and it is understood that many changes and modifications to the described embodiment can be carried out without departing from the scope and the spirit of the invention that is intended to be limited only by the appended claims.

What is claimed is:

1. An objective-type dark-field illumination device for a microfluidic channel, comprising:
   a parallel light source assembly for generating a parallel light;
   an optical stop having a pair of curved slits with respective central points arranged in a direction parallel to an extension direction of a microfluidic channel, wherein the parallel light passes through the two curved slits to generate two curved parallel light; and
   a transmitter objective lens with high numerical aperture (N.A.) for converting the two curved parallel light into two curved conical light focusing on a spot in the microfluidic channel, so as to illuminate tested samples in the microfluidic channel and to lower the light scattering behavior of inner walls of the microfluidic channel, wherein the focused spot size is smaller than the width of the inner walls of the microfluidic channel.

2. The objective-type dark-field illumination device for a microfluidic channel according to claim 1, wherein the size of the two curved slits is equal to each other and the two curved slits are symmetrically arranged on the optical stop.

3. The objective-type dark-field illumination device for a microfluidic channel according to claim 1, wherein each of the two curved slits has two ends by defining an included angle in relation to a geometric center of the optical stop, and the included angle is ranged between 60 and 90 degree.

4. The objective-type dark-field illumination device for a microfluidic channel according to claim 3, wherein the included angle is 80 degree.

5. The objective-type dark-field illumination device for a microfluidic channel according to claim 1, wherein each of the two curved slits has a radial width equal to or smaller than 3 mm.

6. The objective-type dark-field illumination device for a microfluidic channel according to claim 5, wherein the radial width is 2 mm.

7. The objective-type dark-field illumination device for a microfluidic channel according to claim 1, wherein the parallel light source assembly comprises a continuous light source, a condenser lens, a pin-hole stop, a reflective mirror and a field lens in turn.

8. The objective-type dark-field illumination device for a microfluidic channel according to claim 7, wherein the pin-hole stop has a pin-hole, and the diameter of the pin-hole is ranged between 0.1 and 2 mm.

9. The objective-type dark-field illumination device for a microfluidic channel according to claim 8, wherein the diameter of the pin-hole is 1 mm.

10. The objective-type dark-field illumination device for a microfluidic channel according to claim 8, wherein the size of the pin-hole is a factor to determine the focused spot size which is varied by adjusting the size of the pin-hole.

11. The objective-type dark-field illumination device for a microfluidic channel according to claim 1, wherein the N.A. value of the transmitter objective lens is ranged between 0.7 and 1.2.

12. The objective-type dark-field illumination device for a microfluidic channel according to claim 1, wherein an entrance pupil of the transmitter objective lens is ranged between 10 to 20 mm.

13. The objective-type dark-field illumination device for a microfluidic channel according to claim 1, wherein the focused spot size is smaller than 100 μm.

14. The objective-type dark-field illumination device for a microfluidic channel according to claim 1, further comprising a receiver objective lens with low N.A. for receiving scattered light or emitted fluorescent light of the tested samples passed through the microfluidic channel.

15. The objective-type dark-field illumination device for a microfluidic channel according to claim 14, wherein the N.A. value of the receiver objective lens is smaller than that of the transmitter objective lens.

16. The objective-type dark-field illumination device for a microfluidic channel according to claim 15, wherein the N.A. value of the receiver objective lens is ranged between 0.45 and 0.7.

17. The objective-type dark-field illumination device for a microfluidic channel according to claim 14, wherein the receiver objective lens further guides the received scattered light or emitted fluorescent light of the tested samples into an optical detection system.

18. The objective-type dark-field illumination device for a microfluidic channel according to claim 17, wherein the optical detection system is selected from charge-coupled device, photomultipliers, spectrometer or spectrophotometer.

19. The objective-type dark-field illumination device for a microfluidic channel according to claim 18, wherein the optical detection system is a spectrometer or a spectrophotometer, and the parallel light is a light source with continuous wavelength, so that the optical detection system can simultaneously excite and detect the emitted fluorescent signals of at least two fluorescent colors with at least two fluorescent samples.

20. The objective-type dark-field illumination device for a microfluidic channel according to claim 14, wherein the radial width s of the curved slits is determined according to equations (I) and (II), as follows:

$$D_i = 2(N.A.)(f_o) \qquad (I);$$

$$s = (D_o - D_i)/2 \qquad (II);$$

wherein N.A. is an numerical aperture value of the receiver objective lens; $f_o$ is a focal length of the transmitter objective lens; $D_i$ is the calculated entrance pupil of the transmitter objective lens when N.A. is equal to the receiver objective lens or an inner diameter of the curved slits; $D_O$ is the entrance pupil of the transmitter objective lens or an outer diameter of the curved slits; and s is the radial width of the curved slits.

* * * * *